US012805788B1

(12) United States Patent
Sherman

(10) Patent No.: US 12,805,788 B1
(45) Date of Patent: Nov. 24, 2026

(54) SERIES RESISTANCE COMPENSATION WITH CURRENT PREDICTION

(71) Applicant: Adam Jacob Sherman, Montreal (CA)

(72) Inventor: Adam Jacob Sherman, Montreal (CA)

( * ) Notice: Subject to any disclaimer, the term of this patent is extended or adjusted under 35 U.S.C. 154(b) by 0 days.

(21) Appl. No.: 18/963,623

(22) Filed: Nov. 28, 2024

(51) Int. Cl.
*A61B 5/327* (2021.01)
*A61B 5/00* (2006.01)

(52) U.S. Cl.
CPC ............ *A61B 5/327* (2021.01); *A61B 5/7203* (2013.01)

(58) Field of Classification Search
CPC ......... A61B 5/327; A61B 5/7203; H03K 3/11
USPC ......................... 327/530, 538, 540, 541, 543
See application file for complete search history.

(56) References Cited

U.S. PATENT DOCUMENTS

| | | | | |
|---|---|---|---|---|
| 4,510,442 | A | 4/1985 | Neher | |
| 6,163,719 | A | 12/2000 | Sherman | |
| 6,700,427 | B1 | 3/2004 | Sherman | |
| 7,741,829 | B2 | 6/2010 | Tanaka | |
| 8,163,527 | B2 | 4/2012 | Tanaka | |
| 10,393,727 | B2 | 8/2019 | Lobdill | |
| 10,627,357 | B2 | 4/2020 | Lobdill | |
| 10,768,211 | B2 * | 9/2020 | Pupalaikis | G01R 31/40 |
| 12,124,284 | B2 * | 10/2024 | El-Nozahi | G05F 1/577 |

OTHER PUBLICATIONS

Sherman, A. J. et al., “Series Resistance Compensation for Whole-Cell Patch-Clamp Studies Using a Membrane State Estimator”, Biophysical Journal, Nov. 1999, p. 2590-2601, vol. 77—Iss 5, Cell Press, Cambridge MA USA.

Higgins Jr, W.T., “A Comparison of Complementary and Kalman Filtering”, IEEE Trans. Aerospace and Electronic Systems, May 1975, p. 321-325, vol. AES-11, No. 3, IEEE New York, New York, USA.

Sigworth, F.J., “Electronic Design of the Patch Clamp”, Chap 1 of Single-Channel Recording edited by B. Sakmann and E. Neher, 1983, p. 29-32, Plenum Press, New York New York, USA.

“The Axon Guide, Third Edition” edited by Rivka Sherman-Gold, Feb. 2012, p. 86-93, Molecular Devices LLC, Silicon Valley CA, USA.

Moore, J. W. et al., “Compensation for Resistance in Series with Excitable Membranes”, Biophysical Journal, Oct. 1984, p. 507-514, vol. 46—Iss 4, Cell Press, Cambridge MA USA.

* cited by examiner

*Primary Examiner* — Hai L Nguyen

(57) ABSTRACT

One embodiment of a current prediction path (86) for series resistance compensation. A voltage clamp with a series resistance $R_s$ to be compensated comprises a current measurement means (25) that determines a series resistance correction path (87), and a current prediction model (89) that determines the prediction path (86). Correction path (87), accurate at low frequencies, is combined with Prediction path (86), accurate at high frequencies, to form a complemented correction path (88), accurate over low and high frequencies. Complemented path (88) can deliver positive feedback to the voltage clamp, whereby the effective value of the series resistance $R_s$ is decreased. Other embodiments are described and shown.

18 Claims, 6 Drawing Sheets

A

B

A

B

C

SERIES RESISTANCE COMPENSATION WITH CURRENT PREDICTION

BACKGROUND-PRIOR ART

The following is a tabulation of some prior art that presently appears relevant:

U.S. Patents

| Patent Number | Kind Code | Issue Date | Patentee |
|---|---|---|---|
| 10,627,357 | B2 | 2020 Apr. 21 | Lobdill |
| 10,393,727 | B2 | 2019 Aug. 27 | Lobdill |
| 8,163,527 | B2 | 2012 Apr. 24 | Tanaka |
| 7,741,829 | B2 | 2010 Jun. 22 | Tanaka |
| 6,700,427 | B1 | 2004 Mar. 2 | Sherman |
| 4,510,442 | | 1985 Apr. 9 | Neher |

NONPATENT LITERATURE DOCUMENTS

Electronic Design of the Patch Clamp by F. J. Sigworth, 1983, found in Single-Channel Recording, edited by B. Sakmann an E. Neher, Plenum Press, New York, p.29-32.

The Axon Guide, Third Edition. 2012. Molecular Devices Corporation.

A Comparison of Complementary and Kalman Filtering by Walter T. Higgins, Jr., 1975, IEEE Trans. Aerospace and Electronic Systems, Vol. AES-11, no. 3, May 1975.

Ionic current and Electrophysiology

Ionic current—the flow of charged ions in solution-underlies the electrophysiology of many biological cells. Heartbeat generation in cardiac cells, muscle contraction in smooth muscle, nerve signal propagation along axons, neurons firing in the brain: all depend on the flow of ionic current between the intracellular and extracellullar space.

Voltage clamp circuits (FIG. 1A) are widely used to measure such ionic current in single cells. In this arrangement, a voltage source 5 is electrically connected to a cell 15 with an electrode or pipette 10, forming a voltage clamp. Voltage source 5 applies a command voltage $V_e$ to the cell and sources an electrode current $I_p$, which is converted to ions in solutions (the circled "+" and "−" in FIG. 1B). Under these conditions, measuring $I_p$ effectively measures the cellular ionic current.

Voltage Clamp with Series Resistance

In practice, series resistance compromises the measurement of ionic current. Series resistance is a direct consequence of the small physical dimensions of the electrode tip, as is necessary to access a single cell, and it impedes the flow of ionic current. The smaller the tip opening, the higher the value of series resistance, and the more the flow of ionic current is impeded.

Referring to FIG. 1B, electrode 10 comprises an electrode series resistance $R_s$, and an electrode voltage $V_p$; Cell 15 has a membrane capacitance $C_m$ and a cellular ionic current $I_m$ which is modeled by a current generator 20.

When $R_s$ is small enough be ignored, $I_p$ is largely unimpeded and there is negligible voltage drop across $R_s$. Voltage source 5 sets or "clamps" the membrane voltage $V_m$ to $V_e$ and simultaneously shunts $I_m$ which would otherwise flow into $C_m$. In so doing, $I_m$ as produced by current generator 20 is measured and characterized as a function of $V_m$. In practice, however, the large value of $R_s$ (>10 MΩ causes significant voltage drops when ionic current flows, which in turn allows $V_m$ to deviate from the desired clamping voltage.

Since cellular ionic current is often a steep nonlinear function of $V_m$, such voltage deviation will significantly corrupt the measurement of $I_m$.

Series Resistance Compensation

To compensate for series resistance errors, series resistance ($R_s$) compensation (*Sigworth*, p.28)—also know as series resistance correction (*Axon Guide* p.86)—is commonly employed (FIG. 2A). With this technique, a scaled value of the measured electrode current is used as positive feedback to reduce the effective value of $R_s$.

Referring to FIG. 2A, the voltage clamp of FIG. 1B is shown with the addition of a current measurement means 25, a scaler 35, a scaler 36, and a summer 30 having an output voltage $V_{30\_out}$. Measurement means 25 measures the electrode current $I_p$ and outputs a measured electrode current $I_{pmeas}$. Scaler 35 scales $I_{pmeas}$ by a resistance $R_s$ to produce a series resistance correction path 87. Measurement means 25 also acts as a low impedance voltage source, setting the electrode voltage $V_p$ equal to the output of $V_{30\_out}$. Correction path 87 is equal to the current flow of $I_p$ scaled by the resistance value $R_s$, which is also equal to the voltage drop across Electrode 10. Scaler 36 scales Correction path 87 by a scale factor α, where α ranges from 0 to 1, to produce a standard series resistance compensation signal $R_{s\_comp}$. Summer 30 adds $R_{s\_comp}$ to the command voltage $V_e$, and this sum serves as the output signal $V_{30\_out}$, thus forming a positive feedback loop.

The positive feedback provided by Correction path 87 lowers the effective value of the electrode series resistance from $R_s$ to an effective value $R_{eff}$ given by:

$$R_{eff}=(1-a)\cdot R_s \tag{E1}$$

As α is increased, $R_{eff}$ is correspondingly lowered, as per equation E1. This lowers the series resistance voltage errors, and also speeds up the voltage clamp response, allowing faster ionic currents to be measured under voltage clamp conditions.

Limitations of $R_s$ Correction: Instability at high a settings

While it would be desirable to fully compensate for $R_s$ by setting α=1, stability constraints and oscillation onset limit the maximum a attainable. This oscillation limits the utility of $R_s$ compensation in resolving rapid ionic currents. Sigworth shows that this oscillation is related to limited bandwidth of the current measurement circuitry and stray capacitance artifacts of the electrode, both of which severely destabilize $R_s$ compensation when α is set too high (greater than ~ 0.9).

Current Measurement Bandwidth Requirements

Measurement Means 25 has a current measurement bandwidth, which corresponds to the frequency range in which $I_{pmeas}$ follows or mirrors the electrode current $I_p$. In practice, $I_{pmeas}$ follows $I_p$ up to some cutoff frequency, and is attenuated above this cutoff frequency.

It can be shown that as α is increased, the current measurement bandwidth must rapidly increase to maintain stability (see Sigworth, equation 41), and when α approaches 0.9, the achievable current measurement bandwidth becomes limiting. As an illustration, when α>0.9 (90% $R_s$ compensation), the bandwidth of $I_{pmeas}$ must be >300 kHz to maintain stable $R_s$ compensation. Such high bandwidth is very difficult to achieve in practice.

Stray Capacitance and Parasitic Current Artifacts

Even when attempts are made to create a wide bandwidth current measurement-see for example, the "Response-correction circuit" FIG. 1-4, (Sigworth, 1983) or Lobdill's Frequency Boost/Highpass filter 560, or 805, in U.S. Pat. No. 10,393,727 (2019)—they are of limited utility due to another factor which reduces stability at high $R_s$ compensation settings: stray capacitance effects of electrode 10. Electrode 10 has stray capacitance (not modeled in FIGS. 1 and 2) which draws parasitic current at high frequencies. This parasitic current produces measurement artifacts which rapidly destabilize the $R_s$ compensation feedback loop unless these artifacts are canceled. To maintain stability, it is common practice to use capacitance compensation techniques that attempt to cancel or subtract these artifacts from correction path 87, using either analog or digital implementations-see for example, "Fast Transient Cancellation" (Sigworth, p.25). While such subtraction schemes perform reasonably well when paired with a lumped shunt capacitance, the stray capacitance of electrode 10 is in fact distributed along the length of its immersion depth in ways that are both unpredictable and difficult to characterize. The distributed nature of the electrode capacitance becomes more pronounced at higher frequencies, with a corresponding degradation of capacitance compensation effectiveness. Insofar as the cancellation is imperfect-leaving a residual artifact—the maximum attainable series resistance compensation is limited.

Higher Order Capacitance Compensation

With the ultimate aim of improving $R_s$ compensation, various enhancements to capacitance compensation are in use that employ higher order models to provide more accurate or complete artifact cancellation. For example, the Axopath 200B patch clamp amplifier (Molecular Devices Inc., USA) uses a two section RC ladder model with 4 adjustable parameters. Tanaka U.S. Pat. No. 8,163,527 (2012) teaches an automatic tuning scheme with multiple parameter models to cancel capacitive artifacts from a long cable connected to a cell. However, at the high frequencies required for fast $R_s$ compensation, such models strain to maintain stable $R_s$ compensation. Furthermore, at high frequencies, these models are extremely sensitive to slight parameter misadjustments or to shifting experimental conditions as happens, for example, when extracellular bath solution levels change during an experiment. Misadjustments rapidly cause oscillations that kill the cell under study, making such experiments difficult to perform. Consequently, such enhancements to capacitance compensation are insufficient to enable fast $R_s$ compensation that will resolve rapidly ionic current under physiologic conditions.

U.S. Pat. No. 6,700,427

In U.S. Pat. No. 6,700,427 Sherman teaches a frequency selective attenuator (FSA) that attenuates Correction Path 87. The FSA enables 100% $R_s$ compensation to be achieved without oscillations. The FSA eliminates steady state series resistance errors without limiting bandwidth. However, while eliminating steady state errors is useful, the final compensated bandwidth still requires high current measurement bandwidth, with similar limits to the maximum voltage clamp speed attainable. Consequently, the difficulty in resolving high temperature, rapid ionic currents remains remains.

Thus, there exists a need to provide stable $R_s$ compensation that will enable rapid ionic current to be voltage clamped. While prior art techniques exist to compensate for series resistance, they suffer from numerous disadvantages:

(a) they require extremely high current measurement bandwidth that is difficult to achieve and which causes instability;

(b) they require complicated models to cancel high frequency artifacts which are difficult to tune;

(c) they become unstable when parameters shift during an experiment;

(d) they are too slow to resolve rapid ionic currents.

Objects and Advantages

Accordingly, several objects and advantages of the present methods and embodiments are to provide $R_s$ compensation that:

(a) does not require high current measurement bandwidth;

(b) is insensitive to high frequency artifacts, and is that simple to tune;

(c) is insensitive to drifting parameter values over time;

(d) is fast enough to record rapid ionic currents.

A primary object of the present invention is to enable voltage clamping of ionic current in excitable cells. Further objects and advantages of my invention will become apparent from a consideration of the ensuing description and drawings.

SUMMARY

In accordance with several embodiments, a current prediction path is provided that can complement a series resistance correction path of a voltage clamp. The correction path is proportional to a measured electrode current from a current measurement means, whereas the prediction path is proportional to a computed electrode current from a model of the electrode and cell. The model computes said computed electrode current as a function of electrode voltage, and scales the computed electrode current to output a predicted electrode voltage drop. The current prediction path comprises the predicted electrode voltage drop filtered by a complementary filter to the current measurement means. By summing the series resistance correction path, accurate at low frequencies, with the current prediction path, accurate at high frequencies, a complemented correction path is created with very wide bandwidth. The complemented correction path can then be used to deliver positive feedback to the voltage clamp. In so doing, a very fast series resistance correction loop is created.

DRAWINGS-FIGURES

Figure 1:
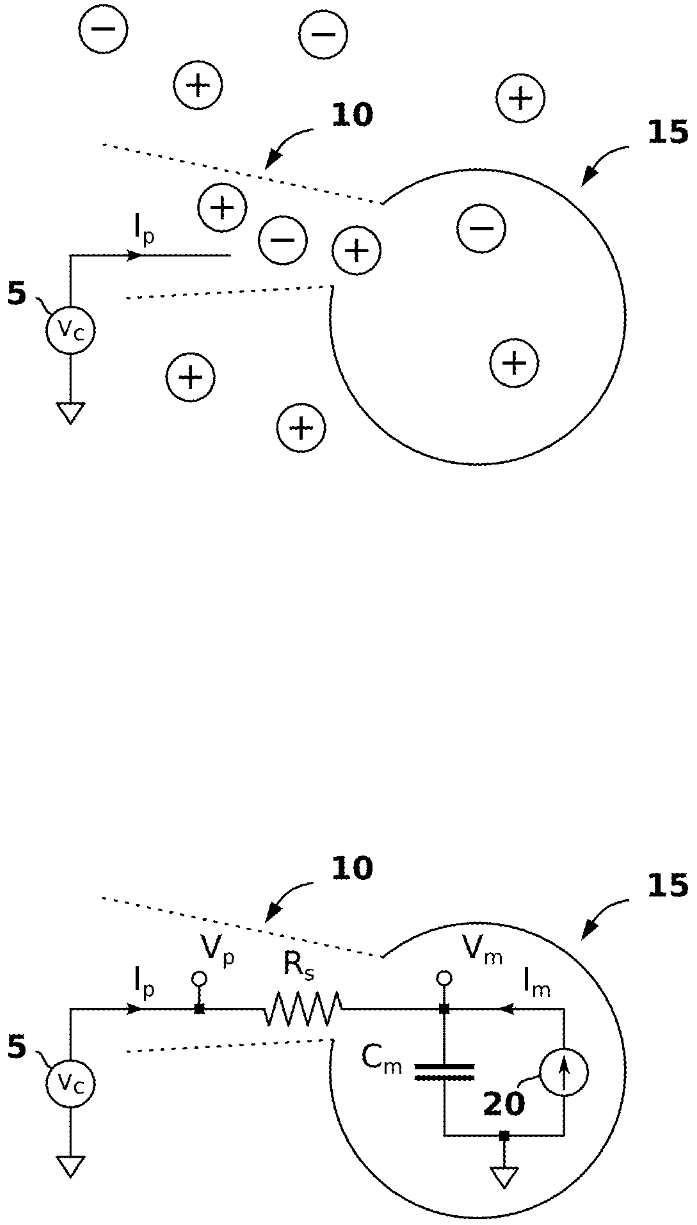
FIG. 1 shows a voltage clamp with an electrode and cell to measure ionic current.

| Drawings-Reference Numerals, labels, and description | | |
|---|---|---|
| 5 | Voltage Source | Command voltage for a voltage clamp. |
| 10 | Electrode | Device to connect a voltage source to a cell. |
| 15 | Cell | |
| 20 | Cellular Ionic Current generator | Models Cellular ionic current to be measured. |
| 25 | Current Measurement Means | Measures the electrode current while presenting a low impedance to the electrode. |
| 30 | Summer | Adds $R_s$ compensation signal to command voltage |
| 35 | Scaler [Units: Ohms] | Scales measured electrode current |
| 36 | Scaler [Units: dimensionless] | Scales $R_s$ Compensation. |
| 86 | Current Prediction Path | Modeled electrode current. Used to complement Series resistance Correction path 87. |
| 87 | Series Resistance Correction Path | Series Resistance Compensation signal. |
| 87.1 | Filtered Correction Path | Correction path 87, filtered by Filter 140 |
| 88 | Complemented Correction Path | Sum of Series Resistance Correction path 87 and Current Prediction path 86. |
| 89 | Current prediction Model | Models the electrode current as a function of electrode voltage, scaled by $R_s$. |
| 89.1 | Complementary Filter | Complementary Filter to Measurement means 25 |
| 89.2 | Predicted Electrode Voltage Drop ($V_{Predicted\_drop}$) | Output of Prediction Model 89. |
| 89.3 | Subtractor | Creates the complement of measurement means 25 by implementing equation E4. |
| 101 | Generalized measurement system | |
| 102 | Generalized measurement system | |
| 103 | subtractor | |
| 104 | Summer | |
| 105 | Equivalent measurement system | Has constant gain transfer function. System reproduces input unaltered. |
| 106 | Paired Measurement System | Paired frequency response to Measurement System 101 |
| 125 | Operational Amplifier | Configured as an I-V converter |
| 125.1 | First Filter | Paired filter to Measurement means 25 |
| 135 | Differential amplifier | Outputs the the measured electrode current scaled by $R_s/R_f$ |
| 135.1 | Differential amplifier | Outputs the the measured electrode current scaled $R_s/R_f$ |
| 135.2 | Frequency Boost means | Increases the bandwidth of Measurement means 25 |
| 135.3 | Operational Amplifier | Configured as a frequency selective differentiator. |
| 140 | Artifact Reduction filter | Lowpass filter to reduce parasitic artifact amplitudes. |
| 140.1 | Second Filter | Paired filter to Artifact Reduction filter 140 |
| 145 | Unity gain buffer | Isolates filter 125.1 from filter 140.1. |
| $\alpha$ | Scaling factor | Ranges between 0 and 1 |
| $C_f$ | Feedback capacitance of I-V converter | |
| $C_m$ | Cell Membrane Capacitance | |
| $f_{cutoff\_140}$ | Cutoff frequency of artifact reduction filter 140 | |
| $I_m$ | Cell Membrane Current | |
| $I_p$ | Electrode Current | |
| $I_{pmeas}$ | Measured Electrode Current. | Output of Current Measurement Means 25 |
| Rf | Feedback resistance of I-V converter | |
| $R_s$ | Electrode Series Resistance | |
| $R_{s\_comp}$ | Fractional Series Resistance | Correction path 87 scaled by $\alpha$. |

-continued

| Drawings-Reference Numerals, labels, and description | | |
|---|---|---|
| | Correction Signal | |
| $\tau_{m1}$ | First paired filter time constant | Value is set roughly equal to $\tau_{z1}$ |
| $\tau_{m2}$ | Second paired filter time constant | Value is set roughly equal to $\tau_{z2}$ |
| $\tau_{z1}$ | Time constant of I-V converter | Equals $R_f \times C_f$ |
| $\tau_{z2}$ | Time constant of Artifact Reduction Filter 140 | |
| $V_c$ | Command Voltage | |
| $V_p$ | Electrode Voltage | |
| $V_m$ | Cell Membrane Voltage | |
| $V_{30\_out}$ | Output of Summer 30 | |

DETAILED DESCRIPTION-FIG. 3A-FIRST EMBODIMENT

Figure 2:
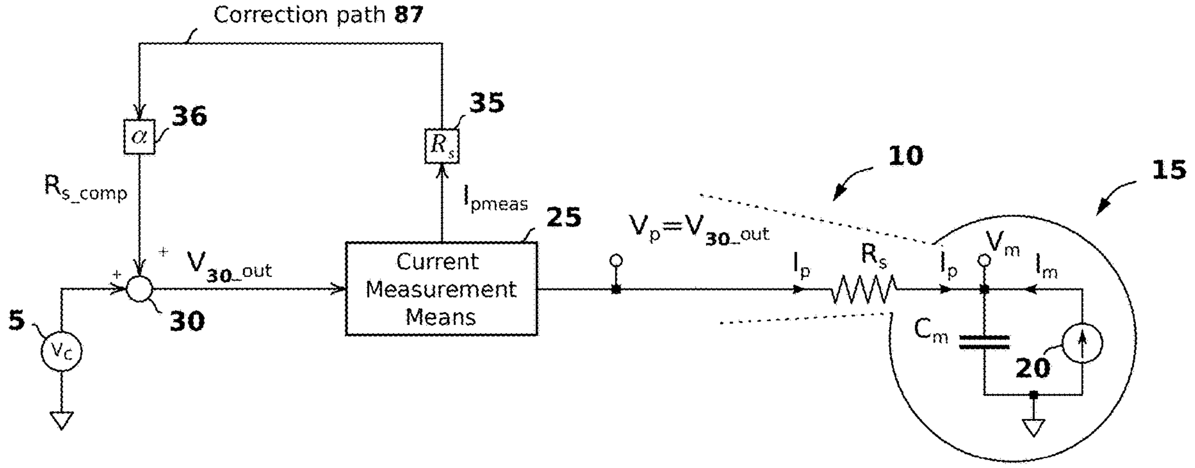
FIG. 2 shows a voltage clamp with Series Resistance ($R_s$) compensation.
Figure 3:
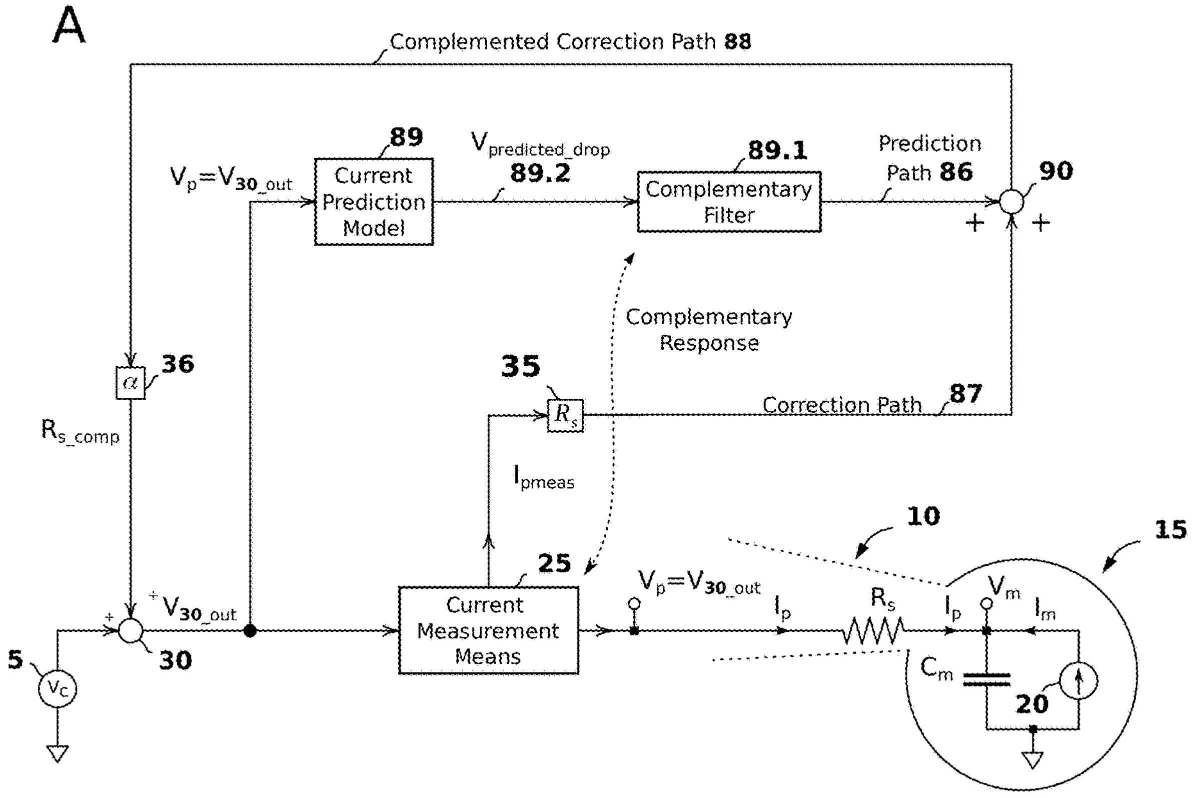
FIG. 3A shows the $R_s$ compensation signal complemented with a Current Prediction Path, in accordance with several embodiments.
FIG. 3B shows the Current Prediction Path implemented using a unity gain buffer and a paired filter, in accordance with one or more embodiments.
Figure 3:
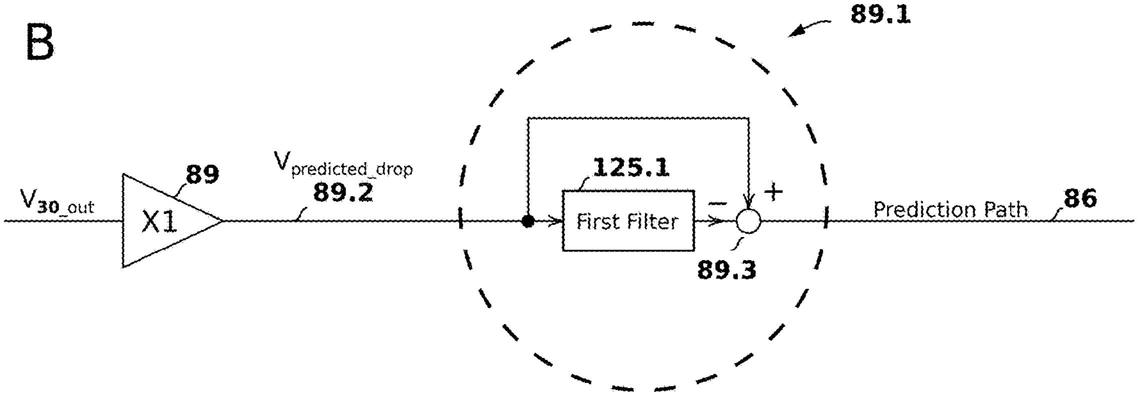

FIG. 3A shows the voltage clamp of FIG. 2, with the addition of a Current Prediction Model 89, a Complementary Filter 89.1, and a summer 90, forming a Complemented Correction Path (CCP) 88, in accordance with the methods and embodiments of the present invention. CCP 88 can then be used in place of Correction Path 87 to implement series resistance compensation, with several ensuing advantages.

Prediction Model 89 takes as input the electrode voltage $V_p$ and calculates a Computed Electrode Current which approximates the current through Electrode 10 as a function of Electrode Voltage $V_p$. Model 89 outputs a Predicted Electrode Voltage Drop 89.2 roughly equal to the Computed Electrode Current scaled by resistance $R_s$. Complementary filter 89.1 filters predicted drop 89.2 with the complimentary filter of Measurement Means 25 (see Equation (4), below, for one of several methods to implement complimentary filter 89.1) and outputs a Current Prediction Path 86. Summer 90 sums Prediction path 86 with Correction Path 87, forming Complemented Correction Path 88. In one embodiment, Model 89 is a follower with roughly constant gain, and Complementary Filter 89.1 comprises a First Filter 125.1 and a Subtractor 89.3 (FIG. 3B). First Filter 125.1 is said to be "paired" to Measurement Means 25 because Filter 125.1 is tuned to have roughly the same frequency response as Current Measurement Means 25. In practice this amounts to matching their frequency responses to within 5%. Tighter matching below 5% results in higher attainable $R_s$ compensation values. Subtractor 89.3 forms the difference voltage between the output of Model 89 minus the output of Model 89 filtered by First Filter 125.1. The output of Subtractor 89.3 serves as Prediction Path 86.

Operation-FIGS. 3A, 3B

Correction Path 87 has an undesired attenuation or signal loss at frequencies above the current measurement bandwidth, and this signal loss compromises series resistance compensation. Prediction Path 86 and Summer 90 serve to "add back" or replace this lost signal and effectively increase the bandwidth of Correction Path 87. This bandwidth increase greatly improves series resistance compensation.

Prediction path 86 adds negligible signal at low frequencies, where Measurement means 25 is accurate, while adding modeled signal at high frequencies to create a nearly ideal $R_s$ compensation signal. Importantly, Prediction path 86 achieves high bandwidth without amplifying parasitic artifacts. In contrast, prior art frequency boost methods do amplify artifacts: the larger the applied boost, the larger amplification. This artifact "feed through" causes positive feedback oscillations and instability which limits the prior art; Prediction path 86 avoids this limitation.

Operation-FIGS. 3A, 3B—Current Prediction path 86

Prior art inextricably links $R_s$ compensation with wide-band current measurement. Prior art teaches (1) that the $R_s$ compensation signal must use the measured electrode current in order to react to unpredictable biological activity; and (2) that the bandwidth of this measured current must be maximized in order to maximize $R_s$ compensation speed and stability.

The insight that underlies the present methods and embodiments is the realization that at the elevated frequencies required for fast $R_s$ compensation, the electrode current has negligible biological component and is in fact fully deterministic. As such, at these frequencies the electrode current need not be measured. It is far better to compute or predict this high frequency current and merge it with a lower frequency measurement where biological activity is present. Doing so overcomes a primary limitation of the prior art: positive feedback instability due to parasitic signal amplification.

Operation-FIGS. 3A, 3B—Current prediction Model 89

A straightforward way to predict the electrode current for Model 89 is to model the electrode and cell combination as a linear passive network and then solve for the transfer function of electrode current versus electrode voltage. This procedure can be applied to FIG. 3A, where the electrode and cell combination (electode 10 connected to cell 15) is modeled as an R-C network. Solving for the required transfer function gives:

$$\frac{R_s I_p(s)}{V_p(s)} = \frac{sR_sC_m}{R_sC_ms+1} \to 1 whens \gg \frac{1}{R_sC_m} \quad \text{(E2)}$$

Equation 2 is a Laplace transform expression for the transfer function of electrode current $I_p$ versus electrode voltage $V_p$, scaled by the electrode series resistance $R_s$. When the Laplace transform frequency variable s is much greater than $$\frac{1}{RsCm},$$

the transfer function approaches unity. Thus at high frequencies the electrode current approaches a constant, and the ideal $R_s$ compensation signal is simply a scaled copy of the input voltage. This corresponds to Current Prediction Model 89 being realized as a constant gain buffer, as in FIG. 3B.

This result can also be seen by inspection of FIG. 3A by recalling that the $R_s$ compensation signal is equal to the IR drop across electrode 10: at high frequency, cell capacitance $C_m$ acts like a short circuit, so the "IR" drop across electrode 10 is simply equal to the electrode voltage $V_p$.

Operation-FIGS. 3A, 3B—Complementary Filter 89.1

Complimentary filter 89.1 of the present methods and embodiments serves to merge a measured signal, accurate at low frequencies, with a computed or predicted signal, accurate at high frequencies. Ideally, the merged signal is then accurate over all frequencies. The implementation of the Complementary filter 89.1 can be understood using the concept of complimentary transfer functions from linear systems analysis. (See, for example, Higgins (1975)).

Figure 4:
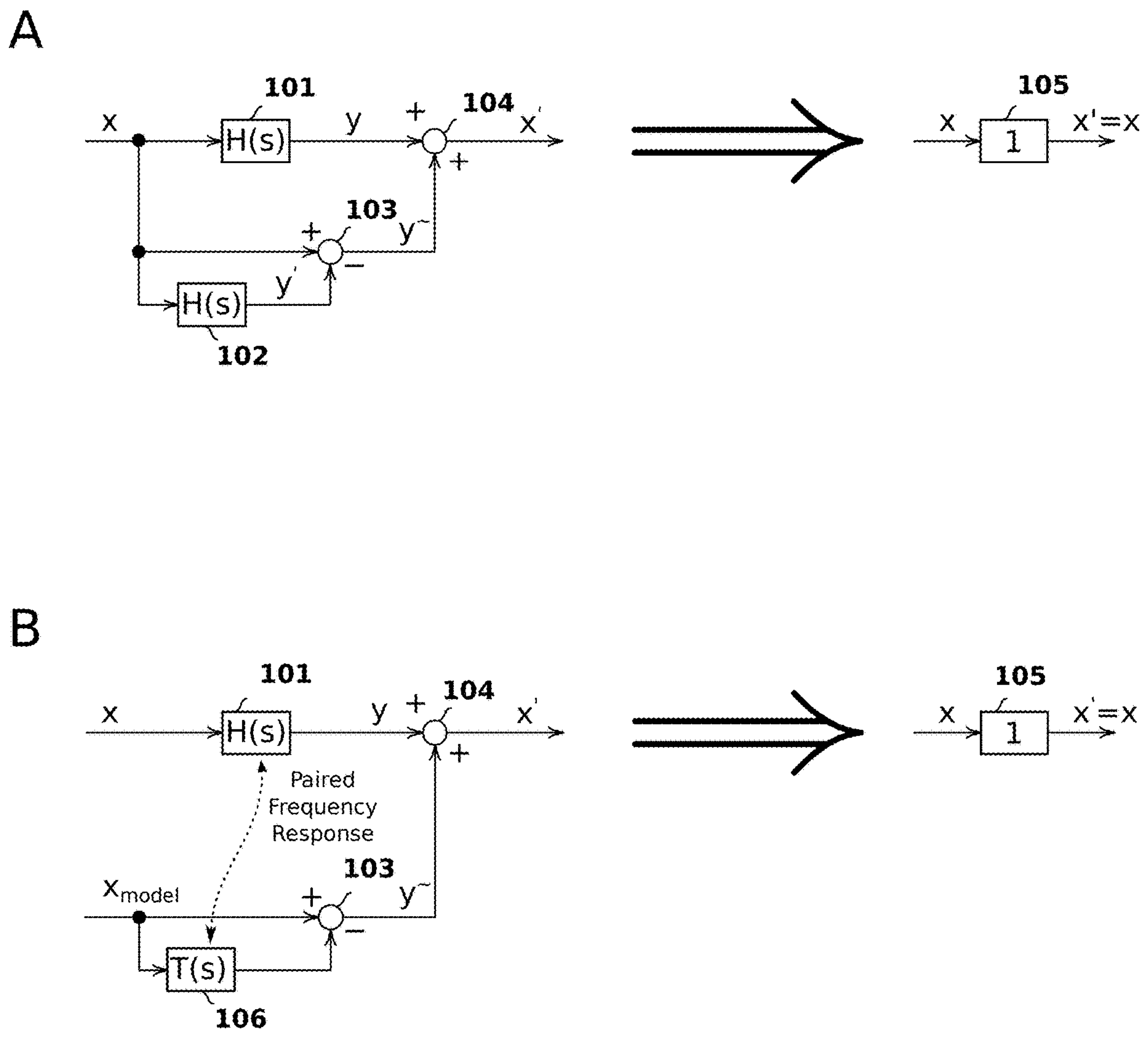
FIG. 4A shows how the bandwidth of a filtered signal can be restored by adding its complement.
FIG. 4B shows how the same bandwidth restoration can also be accomplished using an accurate model of the input signal.

Complementary Transfer Function—General Case, FIGS. 4A and 4B

Given a linear system with a Laplace domain transfer function H(s), the transfer function G(s) is the complement of H(s) if it satisfies the equation $$H(s)+G(s)=1 \quad \text{(E3)}$$

Equation E3 states that adding a system and its complement results in a composite system with a constant gain transfer function. This implies that any input signal processed by such a composite system is transmitted unaltered. This fact is utilized to obtain a wideband signal for $R_s$ compensation in the present methods and embodiments. G(s) can be synthesized be re-arranging equation E3 to create $$G(s)=1-H(s) \quad \text{(E4)}$$

G(s) then implements a complimentary filter to system H(s) such that their transfer functions sum to unity.

Such a composite system is shown in the block diagram of FIG. 4A. A measurement system 101 has a transfer function H(s) with an input a signal x and an output signal y. Signal y serves as a measurement of x, and as such, it accurately follows x up to some bandwidth limit imposed by the system 101, and is attenuated above this bandwidth limit. A parallel system 102, having the same input signal and transfer function as measurement system 101, produces a signal y' which is mathematically equivalent to signal y. A Subtractor 103 implements equation (E4) by outputting a signal $y^{\sim}$ equal to signal x less signal y'. Since signal $y^{\sim}$ satisfies equation (E4), $y^{\sim}$ is the complement of signal y. A Summer 104 adds signal y with signal $y^{\sim}$ and outputs a signal x'. Since summer 104 implements equation (E3), signal x' is equivalent to signal y with no bandwidth limit, and thus signal x' is equal to signal x. This fact is emphasized by an equivalent system 105 on the right which has a transfer function of 1, and thus reproduces the input signal x exactly.

FIG. 4B shows a similar system to FIG. 4A, where the signal $y^{\sim}$ is now formed using an accurate model of the input signal $X_{model}$ in place of the actual signal x, coupled with a "paired" system 106 in place of the parallel system 102. In FIG. 4B, paired system 106 has as input the signal $X_{model}$, and has a transfer function given by T(s). The systems H(s) and T(s) are said to be "paired" when T(s) has roughly the same frequency response as H(s) (emphasized by the dotted line with arrows between systems 101 and 106). Under these circumstances, the output is equivalent to an ideal measurement of the input signal with no bandwidth limit, as in FIG. 4A.

Complementary filter 89.1—The present embodiments

The present embodiments work analogously to the general case shown in FIG. 4B and described above. Measurement Means 25 is analogous to H(s), and adding its complement removes the bandwidth limit of Measurement Means 25. Tuning First Filter 125.1 to have roughly the same frequency response as Measurement Means 25, (matched to within 5% or better) ensures that Prediction Path 86 is a complement signal to Correction Path 87. Therefore, adding prediction path 86 and correction path 87 together forms a wideband signal that effectively removes the bandwidth limit of Measurement Means 25.

Figure 5:
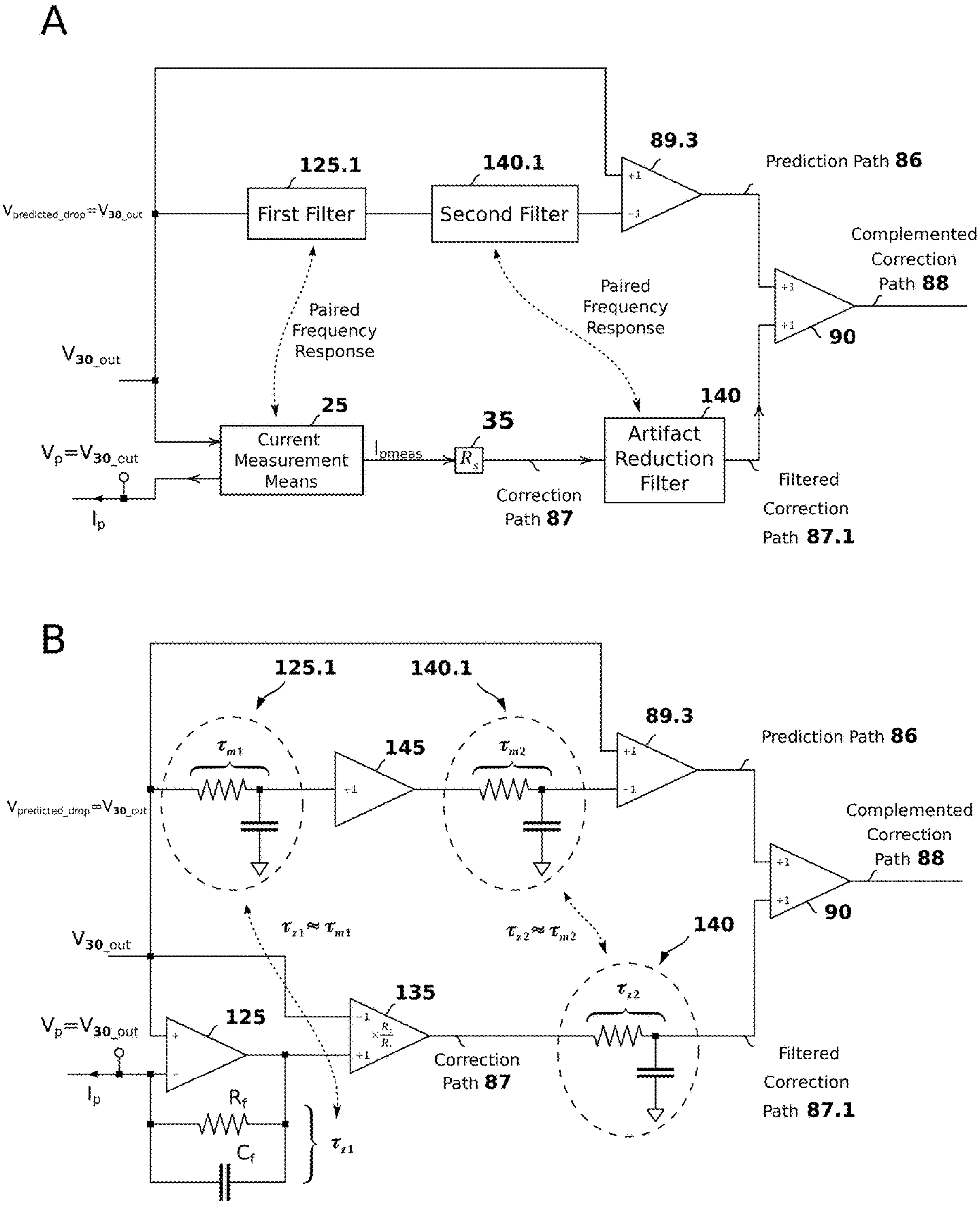
FIG. 5A shows how an Artifact Reduction Filter reduces parasitic signal amplitudes, in accordance with one or more embodiments.
FIG. 5B shows an I-V converter with an Artifact Reduction Filter, in accordance with another embodiment.

Description—FIG. 5A—Embodiment with Artifact Reduction Filter 140

FIG. 5A shows an embodiment where an Artifact reduction filter 140 introduces additional filtering of $I_{pmeas}$. This filtering reduces parasitic artifact feed-through. The embodiment also uses a second Paired filter 141.1 cascaded with first paired filter 125.1 to filter the output of Prediction Model 89.

Referring to FIG. 5A, Correction path 87 is formed by scaling $I_{pmeas}$, as described previously for FIG. 3A. Artifact Reduction Filter 140 then takes as input Correction path 87 and outputs a Filtered Correction Path 87.1. Filtered Correction path 87.1 then serves as an input to Summer 90 in place of Correction path 87.

First Filter 125.1 takes as input voltage $V_{30\_out}$, and the output of Filter 125.1 serves as the input to the second filter 140.1. The output of Second filter 140.1 then serves as the inverting input to Subtractor 89.3.

Operation-FIG. 5A

Reduction filter 140 passes its input signal unattenuated below a cutoff frequency $f_{cutoff\_140}$, and can have a first order or a multi-order attenuation at frequencies above $f_{cutoff\_140}$. Reduction Filter 140 serves to attenuate any residual parasitic signals that could not be fully canceled using Artifact cancellations means (not shown in the Figs) from $I_{pmeas}$. In practice, $f_{cutoff\_140}$ should be high enough to resolve the underling biological signals of interest, with 20-30 kHz usually being sufficient when voltage clamping excitable cells.

First filter 125.1 should be tuned to have roughly the same frequency response as Measurement Means 25 (matched to 5% or better). In this way filter 125.1 and Measurement Means 25 are said to be "paired". Similarly, second filter 140.1 is tuned to have roughly the same magnitude and phase response versus frequency as Reduction Filter 140 (matched to 5% or better), and so filter 140.1 and Reduction Filter 140 are said to be "paired" as well. Note that the cascading order of filters 125.1 and 140.1 is immaterial, so Filters 125.1 and 140.1 can be interchanged with no change in function.

Description—FIG. 5B—I-V Converter Embodiment with Artifact Reduction Filter 140

FIG. 5B shows another embodiment in which Current Measurement Means 25 and scaler 35 are replaced with a Current-to_voltage (I-V) converter implementation, and filters 140, 125.1 and 140.1 are each implemented as passive first order lowpass filters.

Referring to FIG. 5B, an operational amplifier or opamp 125 has a non inverting input terminal, an inverting input terminal, and an output terminal. Opamp 125 acts as a differential amplifier with very high (ideally infinite) gain, and whose input terminals present a very high impedance so as to draw negligible current, the usage of which is well known in the art. $V_{30\_out}$ is connected to the non-inverting terminal, and a negative feedback network consisting of a resistor $R_f$ in parallel with a capacitor Cris connected between the output and inverting terminals of Opamp 125. Opamp 125, together with the feedback network form an I-V converter with a feedback time constant of $\tau_{z1}=R_f*C_f$ and an output signal cutoff frequency given by $$f_{z1} = \frac{1}{2\pi\tau_{z1}}.$$

Negative feedback forces $V_p$ to follow $V_{30\_out}$, and this creates a low impedance node that drives Electrode 10. The I-V converter converts the electrode current $I_p$ to an output voltage given by $I_p*R_f$ with a bandwidth determined by $f_{z1}$, and this voltage is summed with $V_{30\_out}$ by the action of the Opamp 125. A differential amplifier 135, having a gain of roughly $R_s$/Rr outputs the difference of the I-V converter output less the voltage $V_{30\_out}$ so as to isolate the measured electrode current. When diff amp 135 gain is roughly $R_s/R_f$, diff amp 135 output is roughly equal to the voltage drop across electrode 10. Thus the I-V converter together with diff amp 135 serve the same purpose as Current Measurement Means 25 coupled with scaler 35.

Figure 6:
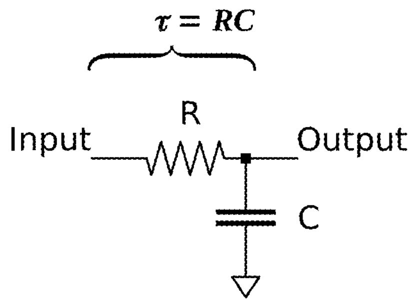
FIG. 6A shows a first order lowpass RC filter.
FIG. 6B shows how the measured current signal bandwidth can be increase using a bandwidth boost means.
FIG. 6C shows an embodiment of a bandwidth boost means using a frequency selective differentiator.
Figure 6:
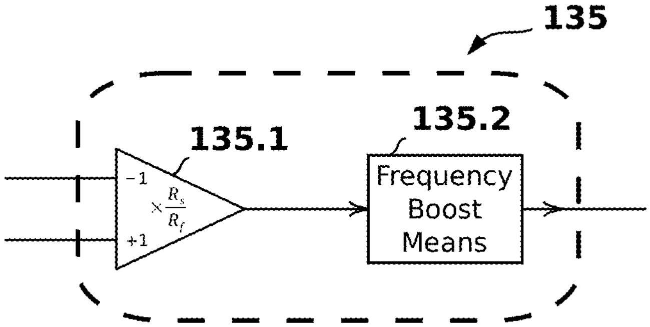
Figure 6:
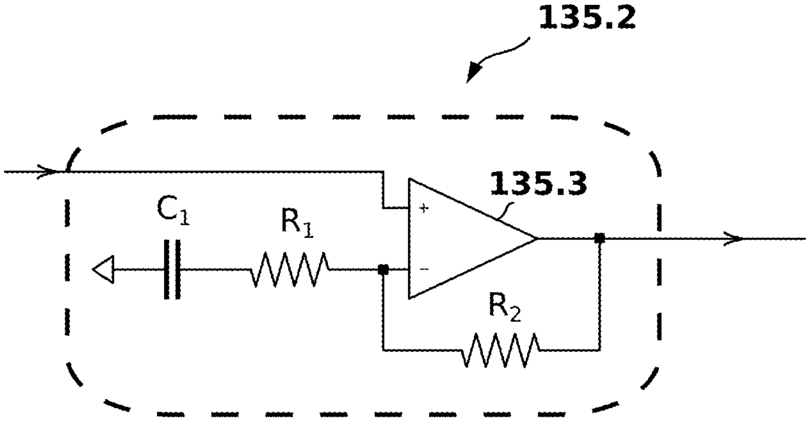

FIG. 5B shows Filters 125.1, 140, and 140.1 each implemented as first order lowpass filters. One such representative filter is shown in FIG. 6A. It comprises a resistor R and a capacitor C in series. R has an input terminal and an output terminal, while C has an output terminal and a ground terminal. The input terminal of R serves as the input of the RC filter. The output terminal of R is connected to the output terminal of C, and this common terminal serves as the output of the RC filter. The ground terminal of C is connected to the ground reference node. The RC filter has a time constant t give by R*C and a cutoff frequency $f_{cutoff}$ given by $$\frac{1}{2\pi\tau}.$$

Referring to FIG. 5B, Filter 125.1 has a time constant $\tau_{m1}$, Filter 140 has a time constant $\tau_{z2}$, and Filter 140.1 has a time constant $\tau_{m2}$. Setting $\tau_{m1}$ roughly equal to $\tau_{z1}$ (within 5%) ensures that Filter 125.1 and the I-V converter (formed with opamp 125) are paired. Similarly, setting $\tau_{m2}$ to be roughly equal to $\tau_{z2}$ (within 5%) ensures that filter 140.1 and Filter 140 are paired as well. This ensures that the paired filter conditions described above for FIG. 5A are also satisfied here. A buffer amplifier 145 having a high input impedance and low output impedance and roughly unity gain can be inserted between filters 125.1 and 140.1 to maintain isolation and to avoid loading effects.

Operation—FIG. 5B

The feedback time constant $\tau_{z1}$ of the I-V converter determines the bandwidth of the measured electrode current $I_{pmeas}$, so $\tau_{z1}$ should be short enough to resolve the signals of interest. When voltage clamping excitable cells such as neurons or cardiac myocytes, $\tau_{z1}$ should be less than ~5 us (~30 kHz bandwidth). It can be challenging to accomplish this because $R_f$ is usually selected to be large (>50 Mohm) to ensure adequate signal to noise (SNR) ratio, while Cr should be greater than ~1 pF to ensure adequate loop-gain of the I-V converter up to a frequency of several Megahertz. The resulting I-V converter feedback time constant of ~50 us ($R_f*C_f$) is then too large; it can then be lowered to ~5 us using a frequency boost means 135.2, as in FIG. 6B, the usage of which is well known in the art.

Referring to 6B, differential amplifier 135 is shown comprising a differential amplifier 135.1 with the same inputs and gain as diff amp 135, and frequency boost means 135.2, which takes as input the output of diff amp 135.1 and boosts the bandwidth of its input signal. Here, the required boost need only increase bandwidth by roughly a factor of 10, which is easy to achieve and does not unduly amplify residual artifacts. This is in marked contrast to prior art methods which require frequency boost factors of several hundred or more, since they are the only means used to achieve a wideband $R_s$ compensation signal.

FIG. 6C shows one embodiment of frequency boost means 135.2 that uses an op amp configured as a frequency selective differentiator. An op amp 135.3 has a resistor R2 connected as a feedback network between the inverting and output terminals of op amp 135.3. A network consisting of a resistor R1 in series with a capacitor C1 is connected between the inverting terminal of opamp 135.3 and system ground. The non inverting terminal of opamp 135.3 serves as the input to frequency boost means 135.2, and the output terminal of opamp 135.3 serves as the output of frequency boost 135.2. To lower the effective value of $\tau_{z1}$, set (R1+R2)*C1 to be roughly equal to $\tau_{z1}$, and then set R1*C1 as the desired lowered effective value time constant.

Advantages Over the Prior Art

From the above description, a number of advantages of some methods and embodiments of the present invention become evident:

Increased Voltage Clamp Speed

The current prediction path realizes a bandwidth of several Megahertz, which in turn greatly increases voltage clamp speed using $R_s$ compensation. These voltage clamps are ~5 to 10 times faster than the prior art, and they readily resolve rapid ionic current in excitable cells.

Simplified Current Measurement Circuitry

The current measurement signal ($I_{pmeas}$) need only resolve the underlying biological activity; unlike the prior art, it does not supply the fast $R_s$ compensation signal. In practice, an $I_{pmeas}$ bandwidth of ~30 kHz is usually sufficient. This modest bandwidth requirement greatly simplifies the current measurement circuitry.

Simplified Artifact Cancellation

Limiting the $I_{pmeas}$ bandwidth effectively filters out high frequency electrode artifacts. Any remaining low frequency artifacts are relatively easy to cancel using a lumped parameter model, and this cancellation is less sensitive to parameter drifting during an experiment. In contrast, prior art uses multi-parameter models that must be carefully tuned in order to cancel high frequency artifacts.

Additional Filtering

A further advantage of the present embodiments is the ability to add higher order lowpass filtering of the $I_{pmeas}$ signal, as needed, without compromising $R_s$ Compensation performance. Such additional filtering can be added explicitly (see, for example, Artifact reduction filter 140, described above), or it can be incorporated in the frequency response of Current Measurement Means 25. This filtering further attenuates electrode artifacts. As long is the additional filtering does not attenuate biological signals of interest, the speed and stability of the $R_s$ compensation remains uncompromised.

Conclusion, Ramifications, and Scope

Accordingly, the reader will see that the present embodiments greatly improves series resistance compensation, with numerous advantages accruing, such as increased speed, ease of construction, and ease of use. Although the above description contains many specificities, these should not be construed as limiting the scope of the invention, but as merely providing illustrations of some presently preferred embodiments. Many other embodiments of the current invention are immediately apparent to one skilled in the art. For example, the complementary filter transfer function in FIGS. 3 and 5 could be solved for directly and implemented as an analog state-variable filter. Alternatively, this transfer function could be implemented digitally using a Field Programmable Gate Array (FPGA), or a suitably fast digital signal processor, equipped with digital-to-analog and analog-to-digital conversion hardware. Furthermore, the present embodiments do not require electrode 10 to be a conventional glass patch pipette or microelectrode to function well. Nor is it required for cell 15 to be a biological preparation. Any electrode used to implement a voltage clamp which has series resistance to be compensated will benefit from the methods taught in the present embodiments.

Thus the scope of the invention should be determined by the appended claims and their legal equivalents, rather than by the examples given.

I claim:

1. A method to compensate for series resistance comprising:

a) providing a voltage clamp connected to a cell through an electrode, said electrode comprising a series resistance, an electrode voltage, and an electrode current;

b) providing a current measurement means that measures said electrode current and outputs a measured electrode current;

c) providing a series resistance correction path proportional to said measured electrode current;

d) providing a current prediction path comprising:

i) providing a current prediction model that takes as input said electrode voltage and outputs a predicted electrode voltage drop;

ii) providing a complimentary filter to said current measurement means that takes as input said predicted electrode voltage drop and outputs said current prediction path; and e) providing a complemented correction path comprising the sum of said series resistance correction path and said current prediction path, wherein said complemented correction path delivers positive feedback to said voltage clamp, whereby said positive feedback lowers the effective values of said electrode series resistance.

2. The method of claim 1, wherein the current prediction model output is proportional to the current prediction model input.

3. The method of claim 1, wherein said complementary filter comprises:

a) providing a first filter paired to the current measurement means;

b) providing, as the first filter input, the predicted electrode voltage drop; and c) providing, as the complementary filter output, the complementary filter input less the first filter output.

4. The method of claim 1, further providing an artifact reduction filter that filters said series resistance correction path, wherein the complementary filter comprises:

a) providing a first filter paired to the current measurement means;

b) providing a second filter paired to the artifact reduction filter;

c) providing, as the first filter input, the complementary filter input;

d) providing, as the second filter input, the first filter output;

e) providing, as the complementary filter output, the complementary filter input less the second filter output.

5. The method of claim 4, wherein the cascading order of the first filter and the second filter is reversed.

6. The method of claim 4, wherein the first filter and the second filter and the artifact reduction filter are first order lowpass filters.

7. The method of claim 1 wherein the current measurement means is an I-V converter.

8. The method of claim 1, further providing a frequency boost means that increases the bandwidth of the current measurement means output.

9. The method of claim 8, wherein the frequency boost means is a frequency selective differentiator.

10. A machine to compensate for series resistance comprising:

a) a voltage clamp connected to a cell through an electrode, said electrode comprising an electrode series resistance, an electrode voltage, and an electrode current;

b) a current measurement means that measures said electrode current and outputs a measured electrode current;

c) a series resistance correction path proportional to said measured electrode current;

d) a current prediction path comprising:

i) a current prediction model that takes as input said electrode voltage and outputs a predicted electrode voltage drop;

ii) a complimentary filter to said current measurement means that takes as input said predicted electrode voltage drop and outputs said current prediction path; and e) a complemented correction path comprising the sum of said series resistance correction path and said current prediction path, wherein said complemented correction path provides positive feedback to said voltage clamp, whereby said positive feedback lowers the effective value of said electrode series resistance.

11. The machine of claim 10, wherein the current prediction model output is proportional to the current prediction model input.

12. The machine of claim 10, wherein said complementary filter comprises:

a) a first filter paired to the current measurement means;

b) the first filter input is the complimentary filter input; and c) the complementary filter output comprises the complementary filter input less the first filter output.

13. The machine of claim 10, further including an artifact reduction filter that filters the series resistance correction path, wherein said complementary filter comprises:

a) a first filter paired to the current measurement means;

b) a second filter paired to the artifact reduction filter;

c) the first filter input is the complimentary filter input;

d) the second filter input is the first filter output;

e) the complementary filter output comprises the complementary filter input less the second filter output.

14. The machine of claim 13, wherein the cascading order of the first filter and the second filter is reversed.

15. The machine of claim 13, wherein the first filter and the second filter and the artifact reduction are first order lowpass filters.

16. The machine of claim 10 wherein the current measurement means is an I-V converter.

17. The machine of claim 10, further including a frequency boost means that increases the bandwidth of the current measurement means output.

18. The machine of claim 17, wherein the frequency boost means is a frequency selective differentiator.

* * * * *